US007572277B2

(12) United States Patent
Roussouly et al.

(10) Patent No.: US 7,572,277 B2
(45) Date of Patent: Aug. 11, 2009

(54) SPINAL OSTEOSYNTHESIS CONNECTOR AND INSTRUMENTATION

(75) Inventors: Pierre Roussouly, Saint Cyr Au Mont D'Or (FR); Daniel Chopin, Groffliers (FR); Laure Bruneau, Paris (FR); Philippe Lemaitre, Alfortville (FR)

(73) Assignee: Warsaw Orthopedic, Inc., Warsaw, IN (US)

( * ) Notice: Subject to any disclaimer, the term of this patent is extended or adjusted under 35 U.S.C. 154(b) by 272 days.

(21) Appl. No.: 10/503,007

(22) PCT Filed: Jan. 30, 2003

(86) PCT No.: PCT/IB03/00301

§ 371 (c)(1),
(2), (4) Date: Feb. 7, 2005

(87) PCT Pub. No.: WO03/063715

PCT Pub. Date: Aug. 7, 2003

(65) Prior Publication Data

US 2005/0154388 A1 Jul. 14, 2005

(30) Foreign Application Priority Data

Jan. 31, 2002 (FR) .................................. 02 01167

(51) Int. Cl.
*A61B 17/70* (2006.01)
(52) U.S. Cl. ...................................... 606/265
(58) Field of Classification Search ................ 606/61, 606/69, 70, 71; 439/224, 293, 783, 801
See application file for complete search history.

(56) References Cited

U.S. PATENT DOCUMENTS

| 4,620,533 | A | * | 11/1986 | Mears | 606/54 |
| 4,920,959 | A | * | 5/1990 | Witzel et al. | 606/53 |
| 5,330,473 | A | * | 7/1994 | Howland | 606/61 |
| 5,620,443 | A | | 4/1997 | Gertzbein | |
| 5,810,817 | A | | 9/1998 | Roussouly et al. | |
| 6,136,002 | A | * | 10/2000 | Shih et al. | 606/61 |
| 6,179,838 | B1 | * | 1/2001 | Fiz | 606/61 |
| 6,575,972 | B1 | * | 6/2003 | Gordon | 606/54 |
| 6,916,319 | B2 | * | 7/2005 | Munting | 606/61 |
| 2002/0029040 | A1 | * | 3/2002 | Morrison et al. | 606/61 |

(Continued)

FOREIGN PATENT DOCUMENTS

FR 2 697 744 A 5/1994
WO WO 2005074824 A1 * 8/2005

*Primary Examiner*—Eduardo C Robert
*Assistant Examiner*—Nicholas Woodall

(57) ABSTRACT

A connector (1) for a spinal osteosynthesis device, for connecting two rods to a plate fixed in a vertebra, includes a first orifice (2) opening onto two opposed faces (3, 4) of the connector (1), and two other orifices (5, 6) opening onto two other opposed faces (7, 8) of the connector (1). Each of the two other orifices (5, 6) are each designed to receive a rod (14, 15) of the osteosynthesis device. The connector (1) includes a mechanism making it possible, when the connector (1) is push-fitted onto a protrusion (100) of a bone anchor member, to tighten the rods (14, 15) simultaneously in the two other orifices (5, 6) when a nut (22) is screwed onto the protrusion (100). An assembly for spinal osteosynthesis device includes a plate (16) that includes a protrusion (100), a connector (1) as previously described, and a nut (22).

9 Claims, 2 Drawing Sheets

U.S. PATENT DOCUMENTS

2002/0128653 A1* 9/2002 Haidukewych ............... 606/69
2004/0147929 A1* 7/2004 Biedermann et al. .......... 606/61
2005/0171537 A1* 8/2005 Mazel et al. .................. 606/61
2006/0106382 A1* 5/2006 Gournay et al. ............... 606/61

* cited by examiner

SPINAL OSTEOSYNTHESIS CONNECTOR AND INSTRUMENTATION

CROSS REFERENCE TO RELATED APPLICATIONS

This application is a National Stage of International Application No. PCT/IB03/00301 filed Jan. 30, 2003, which claims priority to French Application No. FR 02 01167, filed Jan. 31, 2002.

BACKGROUND

The invention generally relates to the field of prostheses for the spinal column, which are intended to correct and stabilize scoliosis or to reposition and stabilize vertebrae in the case of trauma or of a tumour.

Such prostheses, known as "spinal osteosynthesis devices" can be fitted either via the posterior route or by the anterior route. The latter route has, in particular, the feature of allowing direct access to the vertebral bodies, along with many other advantages a summary of which can be found in document FR-A-2 697 744.

Such devices, which allow two or more adjacent vertebrae to be fused together, can be classified into two categories:
- those which employ one or more parts in the form of rigid plates or the like, the plates being fixed to the various vertebrae in the region to be treated; and
- those which employ one or two metal rods fixed along the spinal cord, using appropriate connecting devices.

In the latter category, the devices with two rods are often preferred, because they afford greater stability compared with devices involving one rod, and reduce the risk of lateral deformation. What happens is that the two rods are connected together transversely at least at their two ends, so as to form a frame with an overall rectangular shape. This connection can be achieved either using rigid bars (see document FR-A-2 658 413) or using connectors each having two orifices, one for each rod, in which orifices these rods are immobilized after having been positioned by axial sliding and rotation. The connectors are themselves each fixed to one vertebra.

Document FR-A-2 697 744 discloses one example of a device with two rods connected by connectors as has just been described.

These connectors have the disadvantage of being of a complex design. Above all, fitting them together is a lengthy and relatively complicated process.

Document U.S. Pat. No. 5,620,443 shows an example of a two-rod device, the rods being connected one to each other through transverse connectors, each of which being inserted on the head of a bone screw. Each connector is pressed to the bone screw by a nut, and this pressing causes a deformation of the connector which tends to clamp the rods so that they are locked in their lodgings provided in the connector. The rod clamping quality obtained by this connector depends on the connector's ability to get deformed by the screwing of the nut in the bone screw head.

SUMMARY

One object of the invention is to provide unique instrumentation for spinal osteosynthesis.

Another object of the present invention includes providing a unique connector, instrumentation, or method for spinal osteosynthesis.

Alternatively or additionally, another object is to provide spinal osteosynthesis instrumentation and corresponding methods that use two metal rods connected by transverse connectors of unique design various forms of which are described herein.

Another object of the invention is to propose an instrumentation for osteosynthesis via the anterior route of the type using two metal rods connected by transverse connectors of a simpler design and which are quicker to fit than the existing devices.

To this end, one embodiment of the present application includes a connector for a spinal osteosynthesis device, of the type allowing two rods of the device to be connected simultaneously to a plate fixed into a vertebra, characterized in that:
  it comprises a first orifice opening onto two opposed faces of the connector and two other orifices opening onto two other opposed faces of the connector, each of the other orifices intersecting the first orifice, the two other orifices being designed each to receive a rod of the osteosynthesis device;
  and in that it comprises means making it possible, when the connector is push-fitted via its first orifice onto a protrusion of a bone anchorage member fixed to a vertebra, to tighten the two rods simultaneously inside the two other orifices when a tightening nut is screwed onto the protrusion.

The means allowing the rods to be tightened may comprise a conical bearing surface formed on that part of the first orifice that opens onto the underside of the connector.

The means allowing the rods to be tightened may comprise a washer that can be inserted into that part of the first orifice which opens onto the top face of the connector, the washer comprising a bearing surface intended to collaborate with the nut.

This washer in one form has a rectangular overall shape.

The connector in one form comprises means for immobilizing the washer therein, these means being such as a deformable part of the upper edge of the connector.

Another embodiment of the present application includes an assembly for a spinal osteosynthesis device of the type comprising a bone anchor member intended to be fixed to a vertebra and comprising a protrusion, a connector of one of the types previously described, and a tightening nut which can be screwed onto the protrusion so as simultaneously to immobilize the two rods of the osteosynthesis device.

The connector may be of the type comprising a conical bearing surface and the plate can then comprise, at the base of its protrusion, a frustoconical portion corresponding to the conical bearing surface of the connector.

The bone anchor member may be a plate.

Another embodiment of the invention is a spinal osteosynthesis device of the type comprising, on at least one of its portions, two rods which are secured to the vertebrae via assemblies each formed of a plate fixed into a vertebra and a connector connecting the rods to the plate, characterized in that the assemblies are of the previous type.

As will have been understood, the invention relies on the use of a connecting piece connecting the two rods, the particular construction of which piece allows the two rods to be held simultaneously in position inside the piece, using a single tightening operation which ensures that the rods will be clamped inside the connector, so that the clamping obtained is both quick and optimum.

Another embodiment is directed to a method that includes connecting a vertebra engaging member to a patient's spine. The vertebrae engaging member includes a protrusion with threading. A first rod is placed through a first orifice of a connector, and a second rod is placed through a second orifice of the connector. The protrusion is received through a third orifice of the connector. The first rod, the second rod, the vertebra engaging member, and the connector are clamped together by engaging the threading of the protrusion with a nut. In one form, the nut is tightened to bear against a washer carried in an upper part of the third orifice of the connector. Alternatively or additionally, in another form, the nut is tightened to cause a conical bearing surface of the connector to engage a lower conical portion of the protrusion. Alternatively or additionally, in still another form, the nut includes a first part and a second part that are separated in response to application of an established level of torque to one of these parts as the nut is tightened.

Further objects, embodiments, forms, aspects, features, benefits, and/or advantages will be apparent from the description and drawings provided herewith.

BRIEF DESCRIPTION OF THE DRAWINGS

The invention will be better understood from reading the description which follows with reference to the following appended drawings.

DESCRIPTION OF SELECTED EMBODIMENTS

Figure 1:
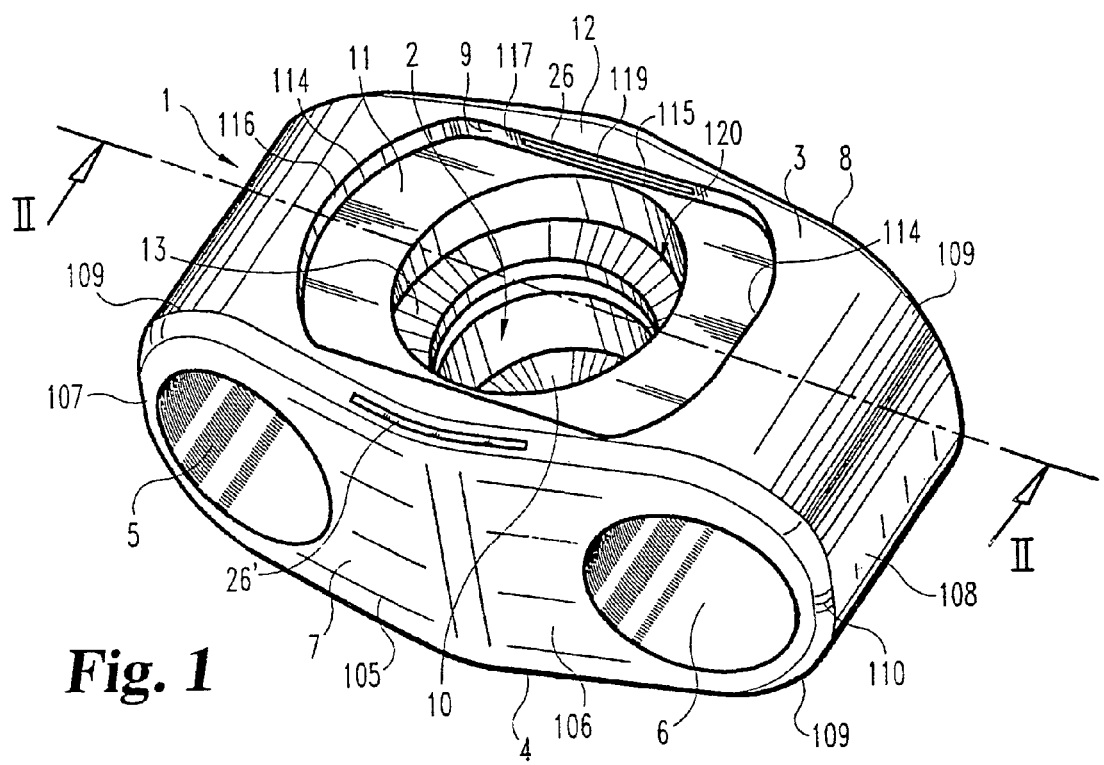
FIG. 1 which, in a perspective view, shows a member for transverse connection of two rods, according to the invention.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the illustrated device, and further applications of the principles of the invention as illustrated or described herein are contemplated as would normally occur to one skilled in the art to which the invention relates.

Figure 2:
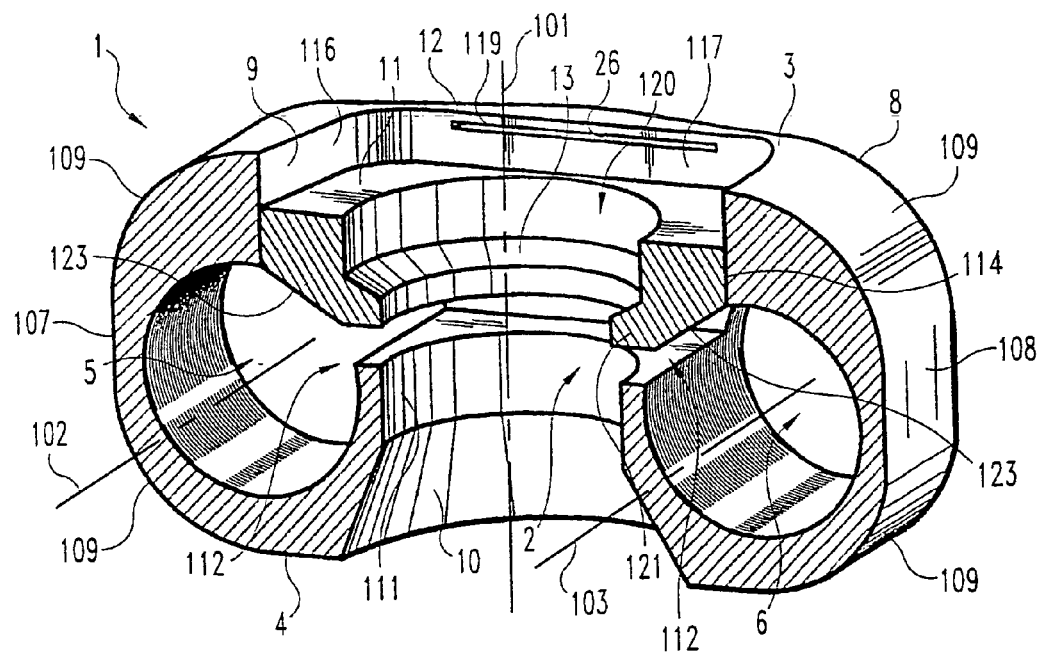
FIG. 2 which shows the FIG. 1 connecting member in perspective and in section along line II-II of FIG. 1.
Figure 3:
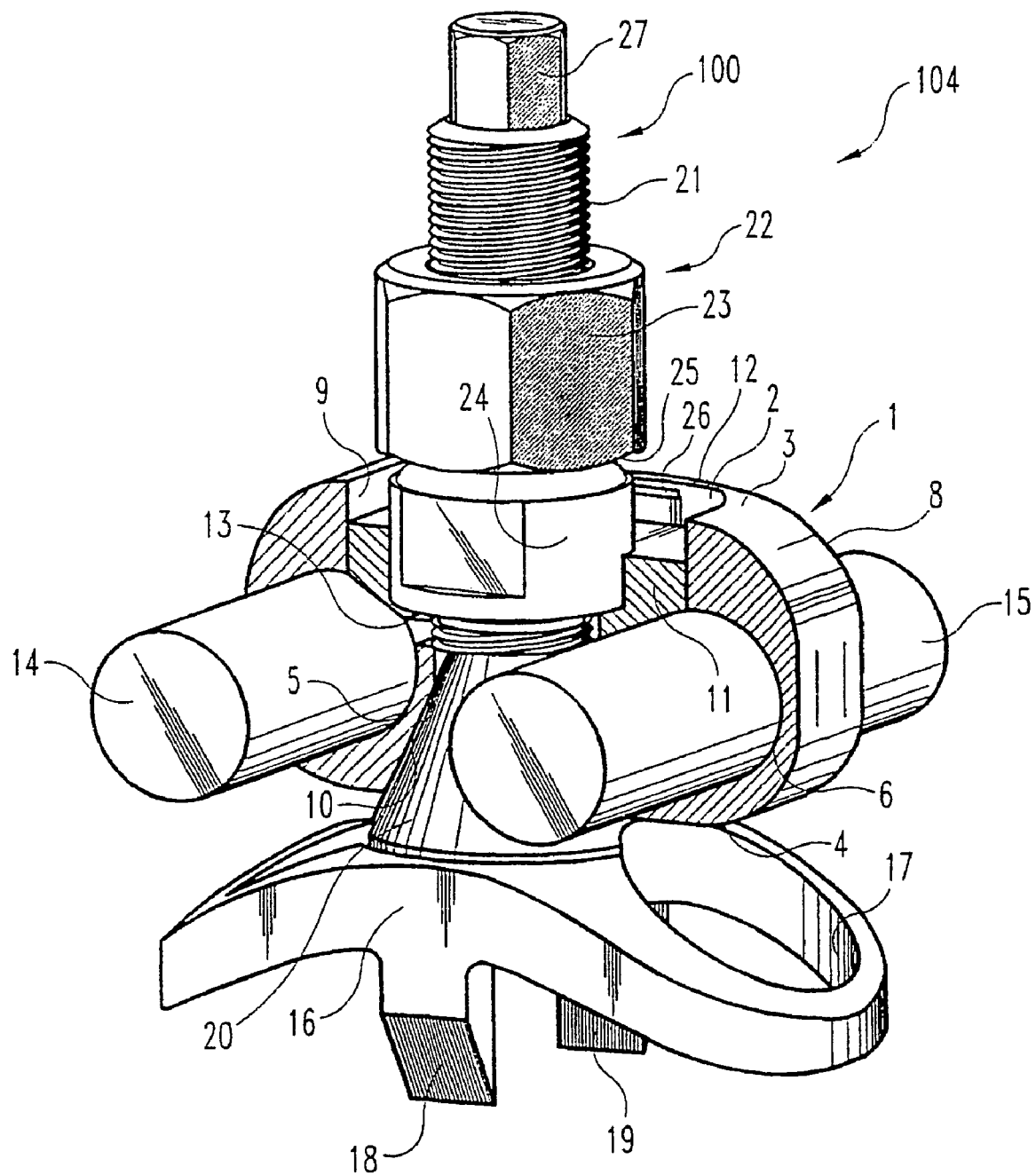
FIG. 3 which, in perspective, depicts the connecting member of FIGS. 1 and 2, as viewed in a section along line II-II, mounted on a plate intended to be fixed to a vertebra, the assembly clamping the two rods of a spinal osteosynthesis device.

One element of a device according to one embodiment of the invention is depicted in isolation in FIGS. 1 and 2. In one embodiment, it includes a connector 1 of paralllepipedal overall shape which may, as shown by the figures, have various rounded and truncated portions intended to limit its bulk. In the illustrated embodiment, as viewed from the top, the connector 1 has a hexagonal cross-sectional shape and as viewed from the front, has an oblong shape. The connector 1 is made of a biocompatible metal material such as a stainless steel or titanium. Three orifices pass right through this connector 1. A first orifice 2 is formed so that it opens more or less at the center of two opposed faces 3, 4 of the connector 1. These faces will be referred to below as the top face 3 and as the underside or bottom face 4. As will be seen, the first orifice 2 allows the connector 1 to be push-fitted onto a protrusion 100 integral with a plate 16 that is fixed to a vertebra (FIG. 3). In FIG. 2, the first orifice 2 is centered around a first axis 101 that extends between the top 3 and bottom 4 face. Two other orifices 5, 6 are formed in such a way as to open onto two opposed faces 7, 8 of the connector 1, which are different than the faces 3, 4 through which the first orifice 2 passes. As shown, opposed or sidewall faces 7 and 8 connect the top face 3 to the bottom face 4. Orifices 5 and 6 are, in principle, arranged roughly symmetrical with respect to the axis 101 of the first orifice 2, and their respective axes 102 and 103 are, in principle, roughly perpendicular to the first axis 101 of the first orifice 2. The two other orifices (rod orifices) 5, 6 are each intended to receive a rod 14, 15 of instrumentation 104 as depicted in FIG. 3, to be more fully described hereinafter.

Between the rod orifices 5, 6, the two opposed faces 7, 8 bow away from one another so as to provide additional support for the first orifice 2 while at the same time reducing the overall size of the connector 1. In particular, each of the two opposed faces 7, 8 has first 105 and second 106 wall portions that are obliquely angled with respect to one another so as to give the two opposed faces 7, 8 the overall bowed appearance. The connector 1 further has lateral wall faces 107 and 108 that connect together both the top 3 and bottom 4 faces as well as faces 7 and 8. As depicted, rounded corner portions 109 are formed between the lateral wall faces 107, 108, and between the top 3 and bottom 4 faces. Referring to FIG. 1, a rounded edge 110 surrounds the two opposed faces 7, 8.

The following features will be noted as regards these various orifices 2, 5 and 6:

each of the rod orifices 5, 6 which is to receive a rod 14, 15 of the instrumentation 104 intersects the first orifice 2;

the first orifice 2 is formed in such a way that its part 9 opens onto the top face 3 of the connector 1 and has an approximately rectangular shape in the example depicted; as to its part opening onto the underside 4 of the connector 1, this is shaped so that it defines a conical bearing surface 10.

Between part 9 of the first orifice 2 and the conical bearing surface 10, the first orifice 2 has a portion 111 that is cylindrically shaped. The configuration of the first orifice 2 allows a washer 11 of corresponding shape to be inserted into its part 9 that opens onto the top face 3 of the connector 1. With reference to FIGS. 1 and 2, part 9 of the first orifice 2 opens into the rod orifices 5, 6 through rod orifices 112, and the washer 11 is received inside part 9 of the first orifice 2. In the illustrated embodiment, the washer 11 has a substantially rectangular shape, as viewed from the top face 3, that generally coincides to the shape of part 9 of the first orifice 2. In particular, the washer 11 has opposing rounded end walls 114 and planar sidewalls 115 that respectively coincide with rounded end portions 116 and planar walls 117 of the first orifice 2. Upper edge 12 of the connector 1 in one embodiment has an overhang region 119 intended to overhang the washer 11 once the latter has been fitted. As shown, a pair of grooves 26, 26' are formed in the overhang region 119 that allow the upper edge 12 of the connector 1 to be deformed. After the washer 11 has been fitted in the first recess 2, a punch can be used to deform the overhang region 119 at the grooves 26, 26' so that the upper edge 12 of the connector 1 protrudes slightly over the washer 11, thereby reducing the chance that the washer 11 will slip, out of the orifice 2 while the connector 1 is being manipulated.

In a recess 120 formed on its top face, the washer 11 has a bearing surface 13, the function of which will be seen later on. Recess 120 in the illustrated embodiment has a generally cylindrical shape, and inside recess 120, a bearing flange 121 with the bearing surface 13 extends radially inwards towards the first axis 101. As shown, the bearing surface 13 on flange 121 is frustoconically shaped in the illustrated embodiment. The washer 11 further has a pair of bevelled rod contacting surfaces 123 that are configured to be received in openings 112 so as to engage the rods 14, 15. In order to press the rod contacting surfaces 123 against the rods 14, 15, a nut 22 can engage the bearing surface 13 of the bearing flange 121.

FIG. 3 depicts a portion of the osteosynthesis instrumentation 104 according to the invention, in the assembled state.

We again see the connector 1 and the washer 11 (these two components, and these alone, being depicted in section on II-II). This connector 1 connects two rods 14, 15 of the instrumentation 104. The connector 1 is mounted on a plate 16, which is intended to be fixed to a vertebra (not depicted) by means of two pedicle screws (not depicted) passing through two orifices 17 each made at one end of the plate 16. Two spikes 18, 19 may be provided for penetrating into the vertebra and improving the attachment of the plate 16. The plate 16 comprises, roughly in its central part, a protrusion 100 onto which the connector 1 can be push-fitted. This protrusion 100 comprises, starting from the plate 16:

a first portion 20 configured as a cone frustum, to the shape of which the conical bearing surface 10 of the first orifice 2 of the connector 1 corresponds;

and a second portion 21 which is a threaded stem onto which a nut 22 can be engaged for immobilizing the instrumentation 104; in the example depicted, the nut 22 comprises two superposed parts 23, 24 separated by a groove 25, the upper part 23 having flats to engage with a tightening tool (not shown) and the lower part 24 having an overall cylindrical shape for allowing rotation of the nut 22 inside the recess 120 in the washer 11.

The instrumentation 104 according to the invention is fitted as follows.

First of all, the plates 16 are fixed to each of the vertebrae concerned. Next, the rods 14, 15 are inserted into the connectors 1. In the instrumentation 104, the number of connectors 1 used correspond to the number of plates 16 that are fixed to the vertebrae. It should be noted that the washers 11 in one embodiment are preloaded in the connectors 1 prior to insertion of the rods 14, 15. After the connectors 1 have been loaded on the rods 14, 15, the connectors 1 are then pushed-fitted onto the protrusions 100 of the plates 16. The precise relative positions of the various members of the instrumentation 104 are then adjusted so as to afford the desired correction to the positions of the vertebrae concerned, then the installation is immobilized by screwing nuts 22 onto each of the protrusions 100 of the plates 16.

It will be understood that as the nuts 22 are screwed on, they come into contact with the bearing surfaces 13 of the washers 11 and cause the washers 11 to exert pressure via surfaces 123 onto the rods 14, 15. At the same time, the conical part 20 of the protrusion 100 of the plate 16 exerts pressure on the conical bearing surface 10 of the connector 1. When the nut 22 is fully tightened, the rods 14, 15 are therefore clamped by the washer 11 and the lower part of the connector 1, and held firmly in the bottoms of the orifices 5, 6. The resistance of the washer 11, which is independent of the remaining part of the connector 1, allows to obtain a very good clamping of the rods 14, 15, though without the need of a particular deformation of the connector 1. So, there are no requirements on the connector's dimensions and on the mechanical properties of its material, which it was necessary to take into account in U.S. Pat. No. 5,620,443 for obtaining a deformation of the connector allowing a good clamping of the rods.

The rectangular shape of the washer 11 in the example depicted gives a relatively large area of contact between the rod contacting surface 123 of the washer 11 and the rods 14, 15, this area being greater than if, for example, the washer 11 had a circular shape. This arrangement typically provides better clamping of the rods 14, 15; however, in other embodiments, a different washer shape may be desired or indeed the washer may be absent, instead providing an integral portion of connector 1 for engagement by nut 22.

As the nut 22 is tightened, in the example depicted, the two parts 23, 24 separate along the groove 25 when a predetermined rupture torque is reached. This rupture torque corresponds to the tightening torque to be achieved and not to be exceeded when fitting the instrumentation 104. The existence of this rupture torque guarantees the value of the torque to which the assembly is tightened, and therefore the resistance slippage (both axially and in terms of rotation) of the rods 14, 15 in the connector 1. Upper end 27 of the second portion 21 of the protrusion 100 of the plate 16 is shaped so that it can be engaged with a screwdriver or equivalent tool which can apply a torque to it. At the upper end 27 of fitting, such a torque is applied so as to break the protrusion 100 along a groove which is not visible in FIG. 3. By virtue of these two operations, it is possible to reduce the bulk of the device once fitting has been achieved.

The use of such a nut 22 which can be broken into two parts 23, 24 is only one alternative form and it would be possible to use a nut made in a single part that could not be broken, without departing from the invention.

One advantage of the invention is that it is possible simultaneously during one single tightening operation, to immobilize the two rods 14, 15 of the instrumentation 104. The fitting time is thereby appreciably reduced.

Furthermore, the invention makes it possible to obtain an effect of simultaneous and parallel distraction on the two rods 14, 15.

Modifications can be made to the device which has just been described without departing from the spirit of the invention. In one example, the presence of the washer 11 is not compulsory, if the dimensions of the device are calculated so as to allow the nut 22 itself to provide the top clamping on the rods 14, 15. In another example, the washer 11 may be replaced by tabs incorporated by design into the connector 1, and on which the nut 22 would exert its pressure so as to cause them to flex and press against the rods 14, 15. The use of the washer 11 as described is, however, an advantageous solution in that:

immobilization by the nut 22 alone could provide an area of contact with the rods 14, 15 that is not desirable in certain situations;

the use of tabs would make the connector 1 more complicated to manufacture, while at the same time introducing risks that these tabs night break during the fitting and use of the device.

Furthermore, the bearing surface 13 formed on the top face of the washer 11 for collaborating with the nut 22 may simply include the flat upper face of the washer 11. Placing the bearing surface 13 in the recess 120 of the washer 11 as depicted in the figures makes it possible to reduce the heightwise bulk of the plate-connector assembly fitted.

The connectors according to the invention and the plates which correspond to it can be used on spinal osteosynthesis devices comprising two rods which are roughly parallel along their entire length.

They can also be used in combination with connector/plate assemblies that take a single rod, in the known case where the spinal osteosynthesis device extends over a high number of vertebrae, and comprises, in succession, one or more portions with two rods and one or more portions with one rod, the latter portions lying in regions where the device is not required to be as rigid.

Furthermore, instead of a plate 16 as described hitherto and depicted in FIG. 3, use may be made of another type of bone anchor member, such as a pedicle screw or a hook.

While the invention has been illustrated and described in detail in the drawings and foregoing description, the same is to be considered as illustrative and not restrictive in character, it being understood that only the preferred embodiment has been shown and described and that all chances, modifications, and equivalents that come within the spirit of the inventions described herein and/or defined by the following claims are desired to be protected.

What is claimed is:

1. A spinal osteosynthesis device, comprising:
a connector defining a protrusion opening extending along an axis and configured to receive a protrusion that is affixed to a vertebra;
the connector defining two rod openings configured to receive rods;
the protrusion opening intersecting the two rod openings to define rod contacting orifices;
a rod contacting member having rod contacting surfaces, the rod contacting surfaces being located in the rod contacting orifices to directly clamp against the rods in the two rod openings of the connector;
wherein the connector defines a groove configured to permit deformation of the protrusion opening for retaining the rod contacting member in the connector;
wherein the connector has a sidewall including the groove;
wherein the groove extends through the sidewall from an outer face of the sidewall and intersecting the protrusion opening in a direction transverse to the axis to define an overhang region of the connector; and
wherein the overhang region is permanently deformed to protrude over the rod contacting member in the protrusion opening.

2. The device of claim 1, wherein the rod contacting member is a washer.

3. A spinal osteosynthesis device, comprising:
a connector defining a protrusion opening extending along an axis and configured to receive a protrusion that is affixed to a vertebra;
the connector defining two rod openings configured to receive rods;
the protrusion opening intersecting the two rod openings to define rod contacting orifices;
a rod contacting member having rod contacting surfaces, the rod contacting surfaces being located in the rod contacting orifices to directly clamp against the rods in the two rod openings of the connector;
wherein the rod contacting member is a washer;
the washer defines a recess with a bearing surface that is frustoconically shaped;
the rod contacting surfaces on the washer are beveled;
wherein the connector has a sidewall including a groove;
wherein the groove extends through the sidewall from an outer face of the sidewall and intersecting the protrusion opening in a direction transverse to the axis;
wherein the groove defines an overhang region of the connector; and
wherein the overhang region is permanently deformed to protrude over the washer in the protrusion opening.

4. The device of claim 3, wherein the washer has a substantially rectangular shape.

5. The device of claim 3, wherein the protrusion opening has a conical bearing surface; and
wherein the protrusion includes a first portion have a cone frustum shape to coincide with the conical bearing surface of the protrusion opening.

6. The device of claim 5, further comprising:
wherein the protrusion includes a second portion that is threaded; and
a nut threaded onto the second portion, wherein the nut includes a first part and a second part that are separated in response to application of an established level of torque to one of these parts as the nut is tightened.

7. The device of claim 3, wherein the two rod openings extend roughly perpendicular to the protrusion opening.

8. A method, comprising:
connecting to a vertebra a vertebra engaging member that includes a protrusion;
placing a first rod through a first orifice of a connector and a second rod through a second orifice of the connector;
inserting the protrusion through a third orifice of the connector extending along an axis;
securing the first rod and the second rod in the connector simultaneously by clamping a rod contacting member that is disposed in the third orifice against the first rod and the second rod;
wherein the rod contacting member is a washer;
wherein the protrusion is threaded;
wherein said securing includes threading a nut on the protrusion to clamp the washer against the first rod and the second rod; and
retaining the rod contacting member in the connector by permanently deforming the connector around the third orifice;
wherein the connector has a sidewall including a groove that extends through the sidewall from an outer face of the sidewall and intersecting the third orifice in a direction transverse to the axis to define an overhang region of the connector; and
wherein said retaining the rod contacting member in the connector includes protruding at least a portion of the overhang region over the washer in the third orifice by permanently deforming the overhang region with a punch.

9. A method, comprising:
connecting to a vertebra a vertebra engaging member that includes a protrusion;
placing a first rod through a first orifice of a connector and a second rod through a second orifice of the connector;
inserting the protrusion through a third orifice of the connector;
securing the first rod and the second rod in the connector simultaneously by clamping a rod contacting member that is disposed in the third orifice against the first rod and the second rod;
wherein the rod contacting member is a washer;
wherein the protrusion is threaded;
wherein said securing includes threading a nut on the protrusion to clamp the washer against the first rod and the second rod; and
retaining the rod contacting member in the connector by permanently deforming the connector around the third orifice, wherein the connector has a groove that defines an overhang region of the connector, and the retaining includes protruding at least a portion of the overhang region over the washer in the third orifice by permanently deforming the overhang region with a punch;
preloading the washer in the connector before said placing a first rod through the first orifice of the connector and the second rod through the second orifice of the connector;
adjusting positions of the first rod and the second rod after said preloading; and
wherein said securing occurs after said adjusting.

* * * * *

UNITED STATES PATENT AND TRADEMARK OFFICE
CERTIFICATE OF CORRECTION

PATENT NO. : 7,572,277 B2
APPLICATION NO. : 10/503007
DATED : August 11, 2009
INVENTOR(S) : Roussouly et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 576 days.

Signed and Sealed this

Fourteenth Day of December, 2010

David J. Kappos
*Director of the United States Patent and Trademark Office*